(12) United States Patent
Rodgers et al.

(10) Patent No.: US 6,747,008 B1
(45) Date of Patent: Jun. 8, 2004

(54) METHODS FOR TREATING AND PREVENTING ALOPECIA

(75) Inventors: Kathleen E. Rodgers, Long Beach, CA (US); Gere S. DiZerega, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/723,255

(22) Filed: Nov. 27, 2000

Related U.S. Application Data

(60) Provisional application No. 60/212,608, filed on Jun. 19, 2000.

(51) Int. Cl.$^7$ ............................................. A61K 38/00

(52) U.S. Cl. .............................. 514/17; 514/2; 514/12; 514/17; 530/324; 424/185.1

(58) Field of Search ................................. 514/2, 17, 12, 514/412, 19, 16, 18, 15, 21; 530/324, 300, 328, 329, 330, 331; 424/185.1

(56) References Cited

U.S. PATENT DOCUMENTS

| | | |
|---|---|---|
| 5,015,629 A | 5/1991 | DiZerega |
| 5,055,456 A | 10/1991 | Harris et al. |
| 5,556,783 A | 9/1996 | Lavker et al. |
| 5,567,679 A | 10/1996 | Daly |
| 5,616,471 A | 4/1997 | Yuspa |
| 5,629,292 A | 5/1997 | Rodgers et al. |
| 5,716,935 A | 2/1998 | Rodgers et al. |
| 5,753,226 A | 5/1998 | Greene et al. |
| 5,804,445 A | 9/1998 | Brasier |
| 5,834,432 A | 11/1998 | Rodgers et al. |
| 5,955,430 A | 9/1999 | Rodgers et al. |
| 5,962,523 A | 10/1999 | Moran et al. |
| 5,977,159 A | 11/1999 | Fandriks et al. |
| 6,096,709 A | 8/2000 | Rodgers et al. |
| 6,110,895 A | 8/2000 | Rodgers et al. |
| 6,177,407 B1 | 1/2001 | Rodgers et al. |
| 6,239,109 B1 | 5/2001 | Rodgers et al. |
| 6,248,587 B1 | 6/2001 | Rodgers et al. |
| 6,258,778 B1 | 7/2001 | Rodgers et al. |
| 6,335,195 B1 | 1/2002 | Rodgers et al. |
| 6,444,646 B1 | 9/2002 | Rodgers et al. |
| 6,455,500 B1 | 9/2002 | Rodgers et al. |
| 6,455,501 B1 | 9/2002 | Rodgers et al. |

FOREIGN PATENT DOCUMENTS

| | | |
|---|---|---|
| JP | 09249535 | 9/1997 |
| WO | WO 98/33813 | 8/1998 |
| WO | WO 99/40107 | 8/1999 |
| WO | WO 99/42122 | 8/1999 |
| WO | WO 99/42123 | 8/1999 |
| WO | WO 00/56345 | 9/2000 |

OTHER PUBLICATIONS

Ngo et al. Computational Complexity, Protein Structure Prediction, and the Levinthal Paradox. Protein Eng. Jun. 1992;5(4):313–21.*
Ambuhl et al. (1994) *Brain Res. Bull.* vol., 35, 289–291.
Bedecs et al., (1997) *Biochem J.*, vol. 325, pp. 449–454.
Bell et al., (1990) *Am. J. Pathol.*, vol. 137, pp. 7–12.
Berk et al., (1989) *Hypertension*, vol. 13, pp. 305–314.
Bryson et al., (1992), *Eur. J. Pharmacol.*, vol. 225, pp. 119–127.
Catalioto et al. (1994) *Eur. J. Pharmacol*, vol. 256, pp. 93–97.
Clouston et al., (1988) *Genomics*, vol. 2, pp. 240–248.
Dzau et al., (1989) *J. Mol. Cell Cardiol.*, vol. 21, pp. S7.
Edwards et al. (1993) *J. Pharmacol. Exper. Ther.* vol. 266, pp. 506–510.
Fernandez et al., (1985) *J. Lab. Clin. Med.*, vol. 1050 pp. 141–145.
Ferrario et al., (1997) *Hypertension*, vol. 30, pp. 535–541.
Ferrario et al, (1998), *J. Am. Soc. Nephrol.*, vol. 9, pp. 1716–1722.
Freeman et al., (1996) *Hypertension*, vol. 28, pp. 104–108.
Helin et al., (1997) *Annals of Medicine*, vol. 29 pp. 23–29.
Iyer et al., (1998) *Hypertension*, vol. 31, pp. 699–705.
Jaiswal et al. (1991) *Hypertension* vol. 17, pp. 1115–1120.
Jaiswal et al. (1992) *Hypertension* vol. 19 (Supp. II):II–49–II–55.
Jaiswal et al. (1993) *J. Pharmacol. Exper. Ther.* vol. 265, pp. 664–673.
Janiak et al., (1992) *Hypertension*, vol. 20, pp. 737–745.
Kageyama et al., (1984) *Biochemistry*, vol. 23, pp. 3603–3609.
Kauffman et al., (1991), *Life Sci.*, vol. 49, pp 223–228.
Kimura, et al., (1992), *BBRC*, vol. 187, pp. 1083–1090.
Kunapuli et al., (1987) *Circulation Research*, vol. 60, pp. 786–790.
LeNoble, et al.,(1991) *Eur. J. Pharmacol.*, vol. 195, pp. 305–306.
Nakahara et al., (1992) *BBRC*, vol. 184, pp. 811–818.
Ohkubo et al., (1983) *Proc. Natl. Acad. Sci.*, vol. 80, pp. 2196–2200.

(List continued on next page.)

*Primary Examiner*—Christopher Tate
*Assistant Examiner*—B. Dell Chism
(74) *Attorney, Agent, or Firm*—McDonnell Boehnen Hulbert & Berghoff

(57) ABSTRACT

The present invention provides improved methods, kits, and pharmaceutical compositions for treating and preventing alopecia in a subject in need thereof by administering an effective amount of angiotensinogen, angiotensin I (AI), AI analogues, AI fragments and analogues thereof, angiotensin II (AII), AII analogues, AII fragments or analogues thereof or AII AT$_2$ type 2 receptor agonists to the subject.

6 Claims, 2 Drawing Sheets

OTHER PUBLICATIONS

Pfeilschifter et al. (1992) Eur. J. Pharmacol. vol. 225, pp. 57–62.

Portsi et al. (1994) Br. J. Pharmacol. vol. 111, pp. 652–654.

Prescott et al., (1991) Am J. Pathol., vol. 139, pp. 1291–1296.

Regoli et al., (1974), Pharmacological Reviews, vol. 26, pp. 69–123.

Rodgers et al. (1997) J. Burn Care Rehab. vol. 18, pp. 381–388.

Shanugam et al., (1995) Am. J. Physiol., vol. 268, pp. F922–F930.

Steckelings et al., (1996) Biochem. Biophys. Res. Commun., vol. 229, pp. 329–333.

Stouffer et al., (1992) Circ. Res., vol. 70, pp. 820–828.

Taubman et al., (1989) J. Biol. Chem., vol. 264, pp. 526–530.

Viswanathan, et al.,(1992), Peptides, vol. 13, pp. 783–786.

Wang et al. (1995) *Zhongguo Zhonglie Linchuang*, vol. 22, pp. 791–794, abstract XP–002164834.

Wolf et al., (1992) Am. J. Pathol., vol. 140, pp. 95–107.

\* cited by examiner

METHODS FOR TREATING AND PREVENTING ALOPECIA

CROSS REFERENCE

This application claims priority to U.S. Provisional Patent Application No. 60/212,608 filed Jun. 19, 2000. This Application is related to co-pending and commonly owned patent application Ser. No. 09/434,746 filed Nov. 5, 1999; Ser. No. 09/264,563 filed Mar. 8, 1999, now U.S. Pat. No. 6,455,500, issued Sep. 24, 2002; and Ser. No. 09/307,940 filed May 10, 1999, now U.S. Pat. No. 6,475,988, issued Nov. 5. 2002.

FIELD OF THE INVENTION

The present invention relates to methods and pharmaceutical compositions for An treating and preventing alopecia in a a patient in need thereof.

BACKGROUND OF THE INVENTION

Hair growth is not continuous, but comprises alternating periods of growth ("anagen"), regression ("categen") and rest ("telogen"). (U.S. Pat. No. 5,055,456, incorporated by reference herein in its entirety) In the scalp, the anagen phase lasts about 6 years and the telogen phase about 4 months. The growth of scalp hair is not synchronous, and the rate of growth is about 0.4 mm per day. About 90 percent of the more than 100,000 scalp hairs are growing (anagen), so that 50 to 100 hairs are shed daily as they are pushed out at the onset of a new hair cycle.

The hair follicle is an epidermal appendage, the lower part of which undergoes cycles of growth and degeneration. (U.S. Pat. No. 5,556,783, incorporated by reference herein in its entirety) During the anagen (the growing phase) of the hair cycle, matrix keratinocytes located in the bulb region grow vigorously, generating cells that differentiate into several distinct hair components including the medulla, cortex and inner root sheath. During catagen, keratinocytes of the lower follicle below the bulge region (the attachment site of the arrector pili muscle) degenerate and the dermal papilla cells (DP; a group of specialized mesenchymal cells) aggregate and become encapsulated by a connective tissue sheath. Through the contraction of this sheath, the DP aggregate ascends and becomes attached to the bottom of the upper (permanent) portion of the follicle (telogen or the resting phase). Finally, a new epithelial growth originates from the bottom of the bulge area; this downgrowth pushes the DP away and reforms a growing bulb.

The in vitro growth potential of different subpopulations of follicular epithelial cells have been studied. (U.S. Pat. No. 5,556,783) Keratinocytes of different portions of human scalp follicles were isolated by microdissection followed by trypsinization and propagated in the presence of 3T3 feeder cells. The results indicate that the upper follicle contains keratinocytes that have in vitro proliferative potential that is significantly higher than those of the lower follicle, the bulb, the sebaceous gland and the epidermis.

Alopecia (hair loss) is a common condition that results from diverse causes. For example, adrenergic alopecia (common baldness) is seen in the vast majority of adult males and is considered physiologic and part of the aging process. (U.S. Pat. No. 5,616,471, incorporated by reference herein in its entirety) Besides the loss of hair, the length and diameter of each hair will be reduced in the adjacent areas even though the follicles remain intact.

Telogen effluvium is a transient, reversible, diffuse shedding of hair in which a high percentage of hair follicles enter the telogen phase prematurely as a result of physical or mental illness. Among the most important factors incriminated are childbirth, high fever, hemorrhage, sudden starvation, accidental or surgical trauma, severe emotional stress, and certain drugs.

Alopecia areata is an immunologic alopecia characterized by the abrupt onset of sharply defined areas of hair loss. In the most severe cases, the scalp will develop total hair loss (alopecia totalis) or the hair loss will involve the whole body surface (alopecia universalis). Most of the patients will run an unpredictable and relapsing course with multiple episodes of hair loss and regrowth. Only about 20 to 30 percent will have a single reversible episode. Regrowth of hair is common within several months, but in many instances is not complete, and relapses are common. Alopecia areata may be associated with autoimmune diseases such as vitiligo, pernicious anemia, collagen disease, and endocrinopathies.

Traumatic alopecia is induced by physical trauma, of which the two most important groups, from the therapeutic standpoint are trichotillomania and alopecia resulting from cosmetic procedures or improper hair care. Trichotillomania is a compulsive habit in which the individual repeatedly pulls or breaks off his or her own hair in a partially conscious state similar to thumb sucking or nail biting. Traumatic alopecia from cosmetic procedures is done consciously in ill-advised individuals and is almost exclusively seen among females. Sometimes this type of alopecia is associated with folliculitis induced by the occlusive effect of the oily cosmetics used in the procedure.

Anagen effluvium is a temporary alopecia caused by the inhibition of mitosis in the hair papilla by certain cytotoxic drugs, leading to constriction of the hair shaft or to complete failure of hair formation. In particular, alopecia frequently occurs in cancer patients who are treated with chemotherapeutic drugs such as cyclophosphamide (CY) and/or irradiation. U.S. Pat. No. 5,962,523 Such agents damage hair follicles which contain mitotically active hair-producing cells. Such damage may cause abnormally slow growth of the hair or may lead to frank loss. While various attempts have been made to protect against alopecia or abnormal rates of hair growth during such treatments, there remains a need for an agent that prevents damage to hair follicles in a safe and effective manner.

Alopecia may also result from nutritional deficiencies and metabolic defects. Caloric deprivation must be very severe to produce hair loss. Increased shedding sometimes occurs after marked weight loss for obesity. Anemia, diabetes, hyper- and hypovitaminosis, and zinc deficiency may also lead to alopecia.

Treatments for androgenetic alopecia have been ineffective in inducing regrowth. The use of cyclic estrogen therapy in females with an estrogen-dominant contraceptive or topical estrogen has been advocated to reduce the rate of hair loss, but results are not impressive. The claim that topical testosterone induces the growth of terminal hairs in bald scalp of males has not been confirmed.

There have been some indications that minoxidil (ROGAINE®., Upjohn), a potent vasodilator, has been effective in causing scalp hair regrowth in patients with androgenetic alopecia, but the results have been mixed.

U.S. Pat. 5,962,523 discloses the use of butyric acid or butyric acid derivatives to protect against hair damage or loss in a mammal as described herein.

Thus, there remains a need in the art for methods of treating and preventing the various types of alopecia.

SUMMARY OF THE INVENTION

In one aspect, the present invention provides methods and kits for treating or preventing alopecia by contacting the cells with angiotensinogen, angiotensin I (AI), AI analogues, AI fragments and analogues thereof, angiotensin II (AII), AII analogues, AII fragments or analogues thereof, ACE inhibitors, or AII $AT_2$ type 2 receptor agonists, either alone or in combination with other alopecia-inhibiting compounds.

DETAILED DESCRIPTION OF THE INVENTION

Figure 1:
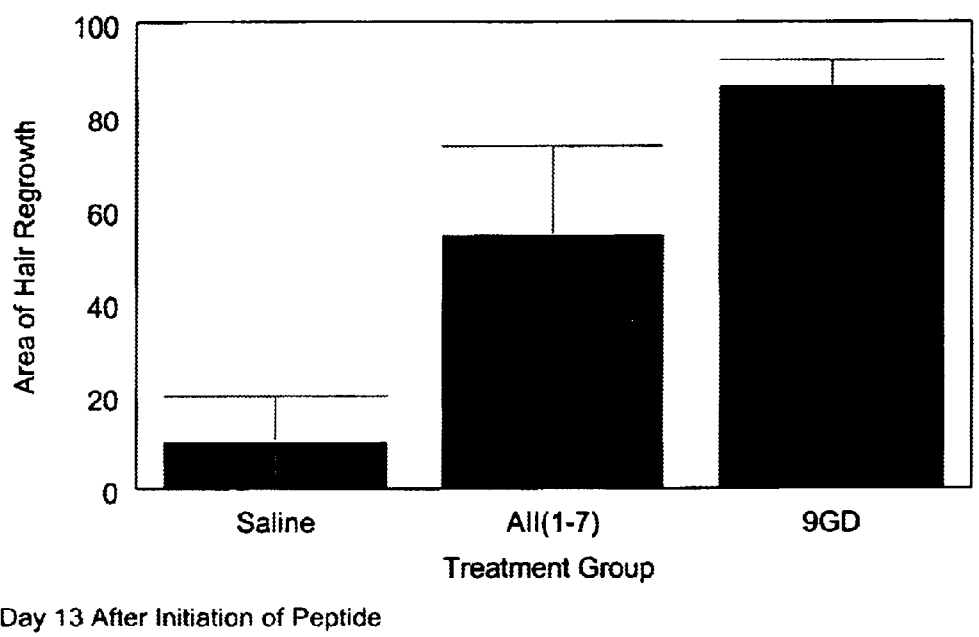
FIG. 1. Effect of angiotensin peptides AII(1–7) and 9GD on hair regrowth after cyclophosphamide treatment.

All cited patents, patent applications and references are hereby incorporated by reference in their entirety.

Unless otherwise indicated, the term "angiotensin converting enzyme inhibitors" or "ACE inhibitors" includes any compound that inhibits the conversion of the decapeptide angiotensin I to angiotensin II, and include but are not limited to alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spiraprii hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. (See for example Jackson, et al., Renin and Angiotensin in Goodman & Gilman's The Pharmacological Basis of Therapeutics, 9th ed., eds. Hardman, et al. (McGraw Hill, 1996); and U.S. Pat. No. 5,977,159.)

Unless otherwise indicated, the term "active agents" as used herein refers to the group of compounds comprising angiotensinogen, angiotensin I (AI), AI analogues, AI fragments and analogues thereof, AII, angiotensin II (AII) analogues, AII fragments or analogues thereof, ACE inhibitors, or AII $AT_2$ type 2 receptor agonists, either alone, combined, or in further combination with other compounds, for treating or preventing alopecia, such as minoxidol, keratinocyte growth factor (KGF), fibroblast growth factor (FGF), epidermal growth factor (EGF), butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from Serratia marcescens), and calcitriol (1,25 dihydroxyvitamin D).

As used herein, "alopecia" refers to hair loss associated with conditions including, but not limited to, adrenergic alopecia, telogen effluvium, alopecia areata, traumatic alopecia, anagen effluvium, and hair loss associated with nutritional deficiencies, metabolic defects, marked weight loss, diabetes, hyper- and hypovitaminosis, and zinc deficiency, alopecia vulgaris, alopecia pustulosa, alopecia erythrodermica, alopecia arthropathica, paraalopecia, palmoplantar pustulosis, all forms of ichthyoses, e.g. ichthyosis vulgaris and congenital ichthyoses, keratodermias of all types, e.g., palmoplantar keratodermia, other genodermatoses with pathological cornification disorders, e.g. Darier's disease, further lichen ruber planus and pityriasis rubra pilaris.

By "treating or preventing alopecia" is meant the ability to cure, reduce or prevent one or more clinical symptoms of alopecia, including, but not limited to, hair loss, cornification, scaling, uneven thickness, persistent itch, inflammation, and rapid epithelial cell turnover in the skin.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (*Circulation Research* 60:786–790 (1987); Clouston et al., *Genomics* 2:240–248 (1988); Kageyama et al., *Biochemistry* 23:3603–3609; Ohkubo et al., *Proc. Natl. Acad. Sci.* 80:2196–2200 (1983)); all references hereby incorporated in their entirety). The substance so formed is a decapeptide called angiotensin I (AI) which is converted to AII by the converting enzyme angiotensinase which removes the C-terminal His-Leu residues from AI, Asp-Arg-Val-Tyr-Ile-His-Pro-Phe-His-Leu [SEQ ID NO:37]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264:526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990)). In addition, AII was shown to be angiogenic in rabbit corneal eye and chick chorioallantoic membrane models (Fernandez, et al., *J. Lab. Clin. Med.* 105:141 (1985); LeNoble, et al., *Eur. J. Pharmacol.* 195:305–6 (1991)).

We have previously demonstrated that angiotensinogen, angiotensin I (AI), AI analogues, AI fragments and analogues thereof, AII, AII analogues, AII fragments or analogues thereof; AII $AT_2$ type 2 receptor agonists are effective in accelerating wound healing and the proliferation of certain cell types, including keratinocytes. See, for example, co-pending U.S. patent application Ser. No. 08/126,370, Filed Sep. 24, 1993; Ser. No. 09/208,337, Filed Dec. 9, 1998; Ser. Nos. 09/108,478, 09/434,746 filed Nov. 5, 1999; Filed Jun. 30, 1998; Ser. No. 09/503,872, Feb. 14, 2000; Ser. No. 08/990,664, Dec. 15, 1997; Ser. No. 09/210,249, Dec. 11, 1998; Ser. No. 09/098,806, Nov. 24, 1998; Ser. No. 09/012,400, Jan. 23, 1998; Ser. No. 09/264,563, Mar. 8, 1999; Ser. No. 09/287,674, Apr. 7, 1999; Ser. No. 09/307, 940, May 10, 1999; Ser. No. 09/246,162, Feb. 8, 1999; Ser. No. 09/255,136, Feb. 19, 1999; Ser. No. 09/245,680, Feb. 8, 1999; Ser. No. 09/250,703, Feb. 15, 1999; Ser. No. 09/246, 525, Feb. 8, 1999; Ser. No. 09/266,293, Mar. 11, 1999; Ser. No. 09/332,582, Jun. 14, 1999; Ser. No. 09/373,962, Aug. 13, 1999; Ser. No. 09/352,191, Jul. 12, 1999; as well as U.S. Pat. Ser. Nos. 5,015,629; 5,629,292; 5,716,935; 5,834,432; and 5,955,430; 6,096,709; 6,110,895; all references herein incorporated in their entirety.

The effect of AII on a given cell type has been hypothesized to be dependent, in part, upon the AII receptor subtypes the cell expresses (Shanugarn et al., *Am. J. Physiol.* 268:F922–F930 (1995); Helin et al., *Annals of Medicine* 29:23–29 (1997); Bedecs et al., *Biochem J.* 325:449–454 (1997)). These studies have shown that AII receptor subtype expression is a dynamic process that changes during development, at least in some cell types. AII activity is typically modulated by either or both the AT1 and AT2 AII receptors. However, AII has recently been shown to stimulate proliferation of primary human keratinocytes via a non-AT1, non-AT2 receptor. (Steckelings et al., Biochem. Biophys. Res. Commun. 229:329–333 (1996)). These results underscore the cell-type (ie: based on receptor expression) specific nature of AII activity.

Many studies have focused upon AII(1–7) (AII residues 1–7) or other fragments of AII to evaluate their activity. AII(1–7) elicits some, but not the full range of effects elicited by AII. (Pfeilschifter, et al., *Eur. J. Pharmacol.* 225:57–62 (1992); Jaiswal, et al., *Hypertension* 19(Supp. II):II-49-II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a, *Br. J. Pharmacol.* 111:652–654 (1994)).

Other data suggest that the AII fragment AII(1–7) acts through a receptor(s) that is distinct from the AT1 and AT2 receptors which modulate AII activity. (Ferrario et al., J. Am. Soc. Nephrol. 9:1716–1722 (1998); Iyer et al., Hypertension 31:699–705 (1998); Freeman et al., Hypertension 28:104 (1996); Ambuhl et al., Brain Res. Bull. 35:289 (1994)). Thus, AII(1–7) activity on a particular cell type cannot be prediieu based solely on the effect of AII on the same cell type. In fact, there is some evidence that AII(1–7) often opposes the actions of AII. (See, for example, Ferrario et al., Hypertension 30:535–541 (1997))

Based on the above, there would be no expectation by one of skill in the art that angiotensinogen, angiotensin I (AI), AI analogues, AI fragments and analogues thereof, AII, AII analogues, AII fragments or analogues thereof, ACE inhibitors, or AII AT$_2$ type 2 receptor agonists could be used to treat or prevent alopecia.

A peptide agonist selective for the AT2 receptor (AII has 100 times higher affinity for AT2 than AT1) is p-aminophenylalanine6-AII ["(p-NH$_2$-Phe)6-AII)"], Asp-Arg-Val-Tyr-Ile-Xaa-Pro-Phe [SEQ ID NO.36] wherein Xaa is p-NH$_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., *BBRC* 187:1083–1090 (1992)).

As hereinafter defined, a preferred class of AT2 agonists for use in accordance with the present invention comprises AII analogues or active fragments thereof having p-NH-Phe in a position corresponding to a position 6 of AII. In addition to peptide agents, various nonpeptidic agents (e.g., peptidomimetics) having the requisite AT2 agonist activity are further contemplated for use in accordance with the present invention.

The active agents of particular interest in accordance with the present invention comprise a sequence of at least three contiguous amino acids of groups $R^1$–$R^8$ in the sequence of general formula I

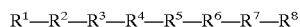

$R^1$ is selected from H, Asp, Glu, Asn, Acpc (1-amninocyclopentane carboxylic acid), Ala, Me$^2$Gly, Pro, Bet, Glu(NH$^2$), Gly, Asp(NH$_2$) and Suc, $R^2$ is selected from Arg, Lys, Ala, Citron, Orn, Ser(Ac), Sar, D-Arg and D-Lys, $R^3$ is selected from the group consisting of Val, Ala, Leu, norLeu, Ile, Gly, Lys, Pro, Aib, Acpc and Tyr;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

In alternate embodiments, the active agents comprise a sequence of at least four, five, six, or seven contiguous amino acids of groups $R^1$–$R^8$ in the sequence of general formula I. In a further alternative, the active agents consist essentially of a sequence of at least four, five, six, or seven contiguous amino acids of groups $R^1$–$R^8$ in the sequence of general formula I.

Compounds falling within the category of AT2 agonists useful in the practice of the invention include the AII analogues set forth above subject to the restriction that $R^6$ is p-NH$_2$-Phe.

Particularly preferred combinations for $R^1$ and $R^2$ are Asp-Arg, Asp-Lys, Glu-Arg and Glu-Lys. Particularly preferred embodiments of this class comprise the following sequences: AII [SEQ ID NO:1], AIII or AII(2–8), Arg-Val-Tyr-Ile-His-Pro-Phe [SEQ ID NO:2]; AII (3–8), also known as des 1-AIII or AIV, Val-Tyr-Ile-His-Pro-Phe [SEQ ID NO:3]; AII(1–7), Asp-Arg-Val-Tyr-Ile-His-Pro [SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII(1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII(4–8), Tyr-Ile-His-Pro-Phe [SEQ ID NO:15] were also tested and found not to be effective.

Another class of compounds of particular interest in accordance with the present invention comprise an amino acid sequence of the general formula II $$R^2—R^3—R^4—R^5—R^6—R^7—R^8$$

in which $R^2$ is selected from the group consisting of H, Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr.

A particularly preferred subclass of the compounds of general formula II has the formula $$R^2—R^3\text{-Tyr-}R^5\text{-His-Pro-Phe [SEQ ID NO:16]}$$

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

Other particularly preferred embodiments comprise the following sequences:

| | | | |
|---|---|---|---|
| 1GD | Ala4-AII(1–7) | DRVAIHP | SEQ ID NO: 38 |
| 2GD | Pro3-AII(1–7) | DRPYIHP | SEQ ID NO: 39 |
| 5GD | Lys3-AII(1–7) | DRKYIHP | SEQ ID NO: 40 |
| 9GD | NorLeu-AII(1–7) | DR(nor)YIHP | SEQ ID NO: 41 |
| GSD 28 | Ile$^8$-AII(1–7) | DRVYIHPI | SEQ ID NO: 42 |
| | Ala3aminoPhe6 AIII: | DRAYIF*PF | SEQ ID NO: 43 |
| | Ala3-AIII | RVAIHPF | SEQ ID NO: 44 |
| | Gly$^1$AII | GRVYIHPF | SEQ ID NO: 45 |
| | NorLeu$^4$-AIII | --RVYnLHPF | SEQ ID NO: 46 |
| | Acpc$^3$-AII | DR(Acpc)YIHPF | SEQ ID NO: 47 |
| GSD 37B | Orn$^2$AII | D(Orn)VYIHPF | SEQ ID NO: 48 |
| GSD38B | Citron$^2$-AII | D(Citron)VYIHPF | SEQ ID NO: 49 |
| 3GD | Pro$^3$Ala$^4$-AII(1–7) | DRPAIHP | SEQ ID NO: 50 |

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me$^2$Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

TABLE 1-continued

Abbreviation for Amino Acids

| | |
|---|---|
| Cit | Citron |
| Orn | Ornithine |

It has been suggested that AU and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$. Alternatively, $R_2$ may be H, Ala, Orn, Citron, Ser(Ac), Sar, D-Arg, or D-Lys.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Lys, Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr (PO$_3$)$_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). It has also been found that $R^4$ can be Ala.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, and Val.

In the angiotensinogen, AI, AI analogues, AI fragments and analogues thereof, AII analogues, fragments and analogues of fragments of particular interest in accordance with the present invention, $R^6$ is His, Arg or 6-NH$_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro or Ala in order to provide the most desirable orientation of R8. In position $R^8$, both a hydrophobic ring and an anionic carboxyl terminal appear to be particularly useful in binding of the analogues of interest to receptors; therefore, Tyr, Ile, Phe(Br), and especially Phe are preferred for purposes of the present invention.

Analogues of particular interest include the following:

TABLE 2

Angiotensin II Analogues

| AII Analogue | Amino Acid Sequence | Sequence Identifier |
| --- | --- | --- |
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr(PO$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by any conventional method, including, but not limited to, those set forth in J. M. Stewart and J. D. Young, *Solid Phase Peptide Synthesis*, 2nd ed., Pierce Chemical Co., Rockford Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. Alternatively, the peptides can be produced by standard molecular biological techniques.

In one aspect of the present invention, a method of treating or preventing alopecia by administering to a patient in need thereof an amount effective to treat or prevent alopecia of angiotensinogen, AI, AI analogues, and/or AI fragments and analogues thereof, AII, AII analogues, AII fragments and analogues thereof, ACE inhibitors, or AII AT$_2$ type 2 receptor agonists, ("active agents"), is disclosed, either alone, combined, or in further combination with other compounds or treatments effective for treating or preventing alopecia, including but not limited to minoxidol, keratinocyte growth factor (KGF), fibroblast growth factor (FGF), epidermal growth factor (EGF), butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from Serratia marcescens), and calcitriol (1,25 dihydroxyvitamin D). In a preferred embodiment, the method is used to limit alopecia in a patient subjected to radiation or chemotherapy treatment.

The active agents may be made up in a solid form (including granules, powders or suppositories) or in a liquid form (e.g., solutions, suspensions, or emulsions), and may be subjected to conventional pharmaceutical operations such as sterilization and/or may contain conventional adjuvants, such as stabilizers, wetting agents, emulsifiers, preservatives, cosolvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

For use in treating or preventing alopecia, the active agents may be administered by any suitable route, including local delivery, parentally, transdermally, or topically in dosage unit formulations containing conventional pharmaceutically acceptable carriers, adjuvants, and vehicles. The term parenteral as used herein includes, subcutaneous, intravenous, intramuscular, intrasternal, intratendinous, intraspinal, intracranial, intrathoracic, infusion techniques or intraperitoneally.

For topical administration, the active agents may be formulated as is known in the art for direct application to a target area. Conventional forms for this purpose include wound dressings, coated bandages or other polymer coverings, ointments, lotions, creams, pastes, jellies, sprays, shampoos, salves, transdermal patches, and aerosols. The percent by weight of the active agent of the invention present in a topical formulation will depend on various factors, but generally will be from 0.005% to 95% of the total weight of the formulation, and typically 1–25% by weight.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emlusifying and suspending agents and sweetening, flavoring and perfuming agents.

The dosage and treatment regimen for treating or preventing alopecia with the active agents is based on a variety of factors, including the age, weight, sex, medical condition of the individual, the severity of the condition, the route of administration, and the particular compound employed. Thus, the dosage regimen may vary widely, but can be on the order of between 0.1 ng/kg and 10 mg/kg of the active agents per body weight are useful for all methods of use disclosed herein, preferably between about 10 ng/kg and 1 mg/kg, more preferably between about 0.1 µg/kg and 200 µg/kg, and most preferably between about 1 µg/kg and 100 µg/kg. For example, treatment of alopecia using the composition may be accomplished by subcutaneous or topical application of the composition to the affected areas one or more times per day for as long as is needed.

In a further aspect, the present invention provides kits for treating or preventing alopecia, wherein the kits comprise an effective amount of the active agents of the invention to treat or prevent alopecia, and instructions for using the amount effective of active agent to treat or prevent alopecia In a preferred embodiment, the kits also contain an effective amount to treat or prevent alopecia of one or more other compounds, including but not limited to minoxidol, keratinocyte growth factor (KGF), fibroblast growth factor (FGF), epidermal growth factor (EGF), butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from Serratia marcescens), and calcitriol (1,25 dihydroxyvitamin D). Effective dosages of the active agents of the invention to treat or prevent alopecia are between about 0.1 ng/kg and 10 mg/kg, as discussed above.

In another aspect of the invention, pharmaceutical compositions are provided that comprise an amount effective to treat or prevent alopecia of one or more of the active agents of the invention in combination with an amount effective to treat or prevent alopecia of minoxidol, keratinocyte growth factor (KGF), fibroblast growth factor (FGF), epidermal growth factor (EGF), butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from Serratia marcescens), and calcitriol (1,25 dihydroxyvitamin D).

EXAMPLE 1

Phase I/II Dose Escalation Study of Angiotensin II 1–7 (AII(1–7) SEQ ID NO:4) Administered Before and After Chemotherapy in Patients with Newly Diagnosed Breast Cancer The Phase I/II study was a prospective, open-label, dose-escalation study comparing the effects of AII(1–7) (SEQ ID NO:4)) in patients with newly diagnosed breast cancer receiving doxorubicin 60 mg/M$^2$ and cyclophosphamide 600 mg/M$^2$ for at least 3 cycles of adjuvant chemotherapy following surgical tumor reduction. A filgrastim comparator arm was used to compare safety and response variables and to assess synergy of AII(1–7) with filgrastim (NEUPOGEN®, Amgen, Inc., Thousand Oaks, Calif.).

Patients who satisfied the inclusion/exclusion criteria received a once daily subcutaneous injection of the given AII(1–7) dose level for 7 days followed by a 1 week rest period prior to any chemotherapy (cycle 0) in the interval between tumor reduction and planned chemotherapy. Dose escalation within an individual patient was not permitted.

Following the rest period, a chemotherapy regimen containing doxorubicin 60 mg/m$^2$ and cyclophosphamide 600 mg/m$^2$ was initiated. AII(1–7) was administered for at least 10 days, or until the absolute neutrophil count (ANC)>1500/µL for 2 days, beginning two days after chemotherapy. Up to three chemotherapy cycles followed by AII(1–7) administration were repeated every 21 days, or as indicated by patient tolerance. Any patient that failed to achieve an ANC>1500/µL by day 15 (13 days of AII(1–7)) received a filgrastim rescue of 5.0 µg/kg/day until the ANC>1500/µL for 2 days.

AII(1–7) (SEQ ID NO:4) Arm:

| | |
|---|---|
| Group 1: | 2.5 µg/kg/day AII(1–7) (0.25 mg/mL) |
| Group 2: | 10.0 µg/kg/day AII(1–7) (1.0 mg/mL) |
| Group 3: | 25.0 µg/kg/day AII(1–7) (5.0 mg/mL) |
| Group 4: | 50.0 µg/kg/day AII(1–7) (5.0 mg/mL) |
| Group 5: | 75.0 µg/kg/day AII(1–7) (10.0 mg/mL) |
| Group 6: | 100.0 µg/kg/day AII(1–7) (10.0 mg/mL) |

Filgrastim Arm:

Filgrastim 5.0 µg/kg/day

During the conduct of the clinical trial to examine the effect of subcutaneous injection of AII (1–7) on hematological recovery in new breast cancer patients receiving chemotherapy (doxorubicin/cyclophosphamide), adverse events that occurred were collected.

An adverse event (AE) was considered any unfavorable or unintended change in structure, function, signs, or symptoms temporally associated with the use of a medicinal product experienced by a person administered a pharmaceutical product, whether or not a causal relationship with the product has been established. During the conduct of this clinical trial, study personnel asked open-ended questions to obtain information about AEs at every visit. Signs and symptoms were graded by the Investigator using the WHO toxicity criteria. For alopecia, no notation was made if there was no hair loss. If there was hair loss, it was graded as mild (1) or pronounced (2). In this trial, the incidents of alopecia associated with chemotherapy were as follows:

| Treatment Group | Historic | AII(1–7) (N = 14) | Filgratim (N = ???) |
|---|---|---|---|
| Alopecia | 77% | 46% | 40% |

These results demonstrate that AII(1–7) significantly decreased alopecia in chemotherapy patients relative to control.

EXAMPLE 2

Hair Follicle Regeneration

Materials: The viscous vehicle was prepared from carboxymethylcellulose (CMC sodium salt, low viscosity, Sigma, St. Louis, Mo., Lot Number 34H0310) consisting of 10% low viscosity CMC in 0.05 M phosphate buffer, pH. 7.2, and sterilized by autoclaving followed by mixing with sterile peptide solutions. For subcutaneous administration, the peptides were dissolved in Lactated Ringers' Solution. AII(1–7) (SEQ ID NO:4) was prepared by Bachem under GMP conditions. 9GD (SEQ ID NO:41) was prepared by the Microchemical Core Laboratory at USC.

Full-Thickness Excision Model

Surgical model: During the experimental period, C57BL/Ksj-db/db diabetic mice (Jackson Laboratories, Cold Spring Harbor, Me.) or Sprague Dawley rats were housed one per cage and maintained in a central animal care facility with a 12-hour light/dark cycle. Water and standard rodent laboratory chow were supplied ad libitum. All animals used for this study received humane care as defined by the National Research Council's criteria for humane care. The study protocols were approved by the University of Southern California's Institutional Animal Care and Use Committee before initiation of the studies.

Mouse Model: On day 0, C57BL/Ksj-db/db diabetic mice were anesthetized with intramuscular ketamine/xylazine and backs were swabbed with 70% isopropyl alcohol followed by betadine. Afterwards, a 1.3 cm diameter full thickness skin area was excised on the back of each mouse. Wound margins were treated with Benzoin Tincture (Western Medical Supply, Arcadia, Calif.).

Rat Model: Female Sprague-Dawley rats, 175 to 200 grams, were anesthetized with intramuscular ketamine/rompun. The backs of the rats were shaved with animal clippers, scrubbed with betadine, and washed with 70% alcohol before surgery. Two 2.25 $cm^2$ excisions, approximately 1 to 2 cm apart, extending to the panniculus carnosus were made mid-dorsally. After treatment, the wounds were covered with a semipermeable polyurethane dressing and the covering was sealed with benzoin solution. Rats were lightly anesthetized with intramuscular ketamine/rompun on day 2 and 4. After anesthesia, the bandages were removed and the area was cleaned before further administration of peptide in 10% carboxymethyl cellulose or by subcutaneous injection.

In the group of animals that received topical medication, immediately after tracing the wound, the various medicaments were administered topically at the wound site through day 4 or by subcutaneous injection daily until necropsy. Wounded areas were covered with Tegaderm transparent dressing (3M Corporation, Minneapolis, Minn.) that was sealed at the edges with Benzoin Tincture. Mice were kept individually. The bandages were changed every 2–3 days through day 14. On day 26 (mice) or day 21 (rats), the animals were euthanized and the wound site was excised en bloc. The tissue was placed in formalin, fixed and prepared for histopathological evaluation.

Microscopic examination of the tissue sections revealed the formation of new adnexal structures in the center of the wound site in animals treated with AII(1–7) and 9GD (Nor Leu 3-AII(1–7)) in both models. This was not observed in placebo treated animals, and was surrounded by epidermis that was undergoing remodeling after formation of new tissue, showing that this occurred at the center of the wound. Various stages of maturation of these new structures could be observed. The most mature structures were identified as new hair follicles by a consulting pathologist.

EXAMPLE 3

Hair Cycle Synchronized Animal Model

Adolescent, 6- to 8-week-old female, C57BL/6 mice (Simonson, Gilroy, Calif.) with normal, black fur were purchased and housed in community cages with 12-hour light cycles with mouse chow and water ad libitum. In contrast to the mosaic cycling of human hair follicles, these mice display a unique hair cycle synchronization, which makes them a most productive model for hair research. Only mice in the resting stage of the hair cycle (telogen) are used for these studies. In the truncal skin of mice all melanocytes reside in hair follicles, and pigment production (melanogenesis) occurs exclusively in anagen follicles. Thus, telogen C57BL/6 mice can be recognized reliably by the homogeneously pink color of their back skin.

Predictable and highly synchronized anagen development can only be achieved with anagen induction by depilation, as opposed to spontaneous anagen development. Thus, anagen was induced in the back skin of telogen mice by depilation so that, at the start of pharmacological manipulation, all hair follicles in the depilated back skin area of all mice are in exactly the same stage of anagen development. As soon as anagen VI had been reached, all mice were injected once with a high dose of cyclophosphamide. In all experiments, control and test mice were then compared for signs of hair loss, for skin color changes indicating the effect of test drugs on hair cycling and follicle melanogenesis, and for hair regrowth.

Anagen VI Induction

Under ketamine hydrochloride-induced general anesthesia, telogen mice that had gone through several postnatal hair cycles were induced to enter anagen by depilation of all telogen hair shafts. This was done by applying a melted wax/rosin mixture to the back skin and by peeling off this mixture after hardening. By this technique, all depilated telogen hair follicles immediately begin to transform into anagen follicles with their associated melanogenesis. This predictably resulted in progressive skin pigmentation and thickening within 5 to 6 days, in the development of mature anagen VI follicles and a gray to black skin color within 8 to 9 days.

Induction of Alopecia

As soon as early anagen VI had been reached by these induced anagen follicles, ie, on day 9 postdepilation (p.d.), a single intraperitoneal injection of cyclophosphamide was given (150 mg/kg).

Chemotherapy induced alopecia was manipulated pharmacologically by administration of the active agents of the present invention, topically or by subcutaneous injection once daily until necropsy. Pigmentation, hair regrowth, and follicle histology are analyzed as indicated. Particular attention is paid to any retarding or enhancing effects on the degree of alopecia, to the hair regrowth pattern, and to the pigmentation of regrowing hair shafts.

Analysis of Chemotherapy Induced Alopecia

After the cyclophosphamide injection on day 9 p.d, the back skin of test and control mice were examined daily for a period of up to 32 days for signs of alopecia and color conversion from black to pink, indicating the progression of anagen follicles in the hair cycle via catagen to telogen. This color change results from the abrupt termination of melanogenesis in follicular melanocytes very early during catagen development. Visible changes were recorded and photodocumented. Starting 1 week after CYP injection, the skin was examined daily for signs of hair regrowth, skin repigmentation, and the quality of hair shaft pigmentation.

In C57BL/6 mice of this age group, depilation induced anagen follicles spontaneously enter catagen between days 17 and 20 p.d., mostly around day 18. The development of catagen follicles was indicated macroscopically by a change in skin color from black to light gray and occurs in large waves, appearing first in the neck region. then on the flanks, until finally the tail region enters catagen. Within 1 to 2 days after catagen induction, the follicle enters telogen, as indicated by a skin color change from gray to pink. Therefore, the alopecia and skin color changes (expressed as percentage of mice with alopecia or in catagen) are recorded separately for two distinct skin regions: region 1: lower quarter of paravertebral back skin above the insertion of the tail: region 2: upper quarter of paravertebral back skin (neck region).

Histological morphometry was performed to check whether the visible changes in skin pigmentation truly reflected changes in hair follicle cycling and not only isolated peptide effects on melanogenesis, and to classify and quantity the follicle subpopulations in a given skin area during the course of experimentation. For histology, back skin from defined skin regions was harvested from test and control mice sacrificed by $CO_2$ inhalation during defined time points. To obtain longitudinal sections through the hair follicles, full-thickness skin was harvested at the level of the subcutis perpendicular to the paravertebral line. Skin was fixed in 5% buffered formaldehyde and processed for routine histology (paraffin embedding, Giemsa stain).

Morphometrical analysis and photography of Giemsa-stained skin sections were performed at 100 to 400× magnification under a Leitz microscope. Follicles were classified according to their hair cycle stages and the percentage of follicles in normal anagen VI or normal catagen was recorded. Because cyclophosphamide administration induces both premature catagen development and dystrophic forms of anagen and catagen in humans, the percentages of both dystrophic follicle phenotypes werre also assessed.

Figure 2:
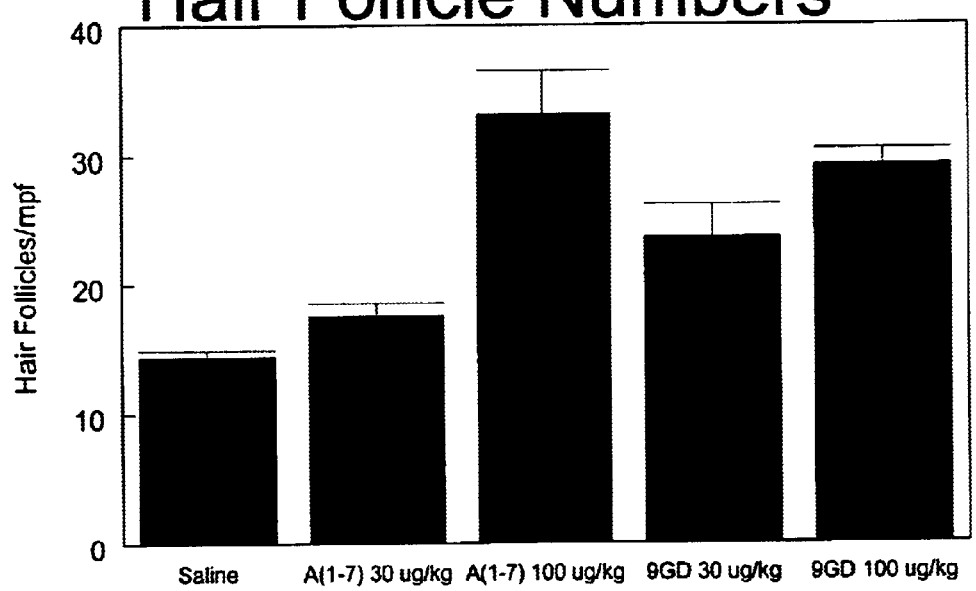
FIG. 2. Effect of angiotensin peptides AII(1–7) and 9GD on hair follicle numbers.

The amount of hair regrowth was evaluated on day 13. As expected, only 1 of 5 control mice had hair regrowth by this day. At this time point, 4 of 5 mice treated with AII(1–7) (30 µg/kg/day) and 5 of 5 mice treated with 9GD (30 µg/kg/day) had observable hair regrowth. The percentage of the area with hair regrowth at this time point was significantly increased (FIG. 1). On day 19, the mice were sacrificed and the tissue placed in formalin for preparation for histological evaluation. The number of mature hair follicles present was also increased by administration of the peptides (FIG. 2).

We claim:

1. A method for treating alopecia, comprising administering to a subject in need thereof at least one active agent comprising a sequence of at least seven contiguous amino acids of groups $R^1$–$R^8$ in the sequence of general formula I $$R^1\text{---}R^2\text{---}R^3\text{---}R^4\text{---}R^5\text{---}R^6\text{---}R^7\text{---}R^8$$

wherein $R^1$ is selected from the group consisting of H, Asp, Glu, Asn, Acpc (1-aminocyclopentane carboxylic acid), Ala, Me$^2$Gly, Pro, Bet, Glu(NH$_2$), Gly, Asp(NH$_2$) and Suc, $R^2$ is selected from the group consisting of Arg, Lys, Ala, Orn, Ser(Ac), Sar, D-Arg and D-Lys;

$R^3$ is selected from the group consisting of Val, Ala, Leu, Lys, norLeu, Ile, Gly, Pro, Aib, Acpc and Tyr;

$R^4$ is selected from the group consisting of Tyr, Tyr(PO$_3$)$_2$, Thr, Ser, Ala, homoSer and azaTyr;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

2. The method of claim 1 wherein the active agent consists of a sequence of at least seven contiguous amino acids of groups $R^4$–$R^8$ in the sequence of general formula I.

3. The method of claim 1 wherein the active agent comprises the sequence SEQ ID NO:41.

4. The method of claim 1 wherein the active agent consists of the sequence SEQ ID NO:41.

5. The method of claim 1 wherein the alopecia is associated with a disorder selected from the group consisting of adrenergic alopecia, telogen effluvium, alopecia areata, traumatic alopecia, anagen effluvium, nutritional deficiencies, metabolic defects, marked weight loss, diabetes, hypervitaminosis, hypovitaminosis, zinc deficiency, alopecia vulgaris, alopecia pustulosa, alopecia erythrodermica, alopecia arthropathica, para-alopecia, palmoplantar pustulosis, ichthyoses, keratodermias, and genodermatoses with pathological cornification disorders.

6. The method of claim 1 further comprising treating the subject with an amount effective of another compound for treating alopecia, selected from the group consisting of minoxidol, keratinocyte growth factor, fibroblast growth factor, epidermal growth factor, butyric acid and its derivatives, ammonium trichloro(dioxy ethylene-0,0') tellurate, interleukin 1, prostaglandin E2, cyclosporine A, corticosteroids and calcitriol.

* * * * *

SEQUENCE LISTING

```
<160> NUMBER OF SEQ ID NOS:  50

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
  1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)
```

-continued

```
<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
 1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8

Asp Arg Val Tyr Ile His
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10
```

```
Asp Arg Val Tyr
  1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
  1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<221> NAME/KEY: MOD_RES
<222> LOCATION: (2)
<223> OTHER INFORMATION: Nle

<400> SEQUENCE: 12

Arg Xaa Tyr Ile His Pro Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<221> NAME/KEY: MOD_RES
<222> LOCATION: (4)
<223> OTHER INFORMATION: Nle

<400> SEQUENCE: 13

Arg Val Tyr Xaa His Pro Phe
  1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
  1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
  1               5

<210> SEQ ID NO 16
<211> LENGTH: 7
<212> TYPE: PRT
```

```
<213> ORGANISM: Artificial Sequence
<220> FEATURE:
<223> OTHER INFORMATION: Description of Artificial Sequence:AII analogue
      class
<221> NAME/KEY: UNSURE
<222> LOCATION: (1)
<223> OTHER INFORMATION: Xaa at position 1 can be Arg, Lys, Ala, Orn,
      Ser, MeGly, D-Arg, or D-Lys
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

Arg Val Tyr Ala His Pro Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
 1               5

<210> SEQ ID NO 21
<211> LENGTH: 11
```

```
<212> TYPE: PRT
<213> ORGANISM: Artificial Sequence
<220> FEATURE:
<223> OTHER INFORMATION: Description of Artificial Sequence:AII analogue
      3

<400> SEQUENCE: 21

Ala Pro Gly Asp Arg Ile Tyr Val His Pro Phe
 1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII analogue
      6

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue
      7

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue
      8

<400> SEQUENCE: 26

Asp Arg Val Tyr Leu His Pro Phe
```

```
                        1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
      10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
```

```
              14
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<221> NAME/KEY: MOD_RES
<222> LOCATION: (3)
<223> OTHER INFORMATION: Nle

<400> SEQUENCE: 33

Asp Arg Xaa Tyr Ile His Pro Phe
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<221> NAME/KEY: MOD_RES
<222> LOCATION: (5)
<223> OTHER INFORMATION: Nle

<400> SEQUENCE: 34

Asp Arg Val Tyr Xaa His Pro Phe
  1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence:
      p-aminophenylalanine 6 AII
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
  1               5
```

```
<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

Asp Arg Val Tyr Ile His Pro Phe His Leu
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:
      1GD:Ala4-AII(1-7)

<400> SEQUENCE: 38

Asp Arg Val Ala Ile His Pro
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: 2GD
      Pro3-AII(1-7)

<400> SEQUENCE: 39

Asp Arg Pro Tyr Ile His Pro
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: 5GD Lys
      3-AII(1-7)

<400> SEQUENCE: 40

Asp Arg Lys Tyr Ile His Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: 9GD
      Norleu-AII(1-7)
<221> NAME/KEY: MOD_RES
<222> LOCATION: (3)
<223> OTHER INFORMATION: Nle

<400> SEQUENCE: 41

Asp Arg Xaa Tyr Ile His Pro
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence GSD28
```

Ile8-AII

<400> SEQUENCE: 42

Asp Arg Val Tyr Ile His Pro Ile
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:
      Ala3aminoPhe6-AII
<221> NAME/KEY: MOD_RES
<222> LOCATION: (6)
<223> OTHER INFORMATION: aminophenyalanine

<400> SEQUENCE: 43

Asp Arg Ala Tyr Ile Xaa Pro Phe
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Ala3-AIII

<400> SEQUENCE: 44

Arg Val Ala Ile His Pro Phe
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:Gly1-AII

<400> SEQUENCE: 45

Gly Arg Val Tyr Ile His Pro Phe
 1               5

<210> SEQ ID NO 46
<211> LENGTH: 8
<212> TYPE: PRT
<213> ORGANISM: Artificial Sequence
<220> FEATURE:
<221> NAME/KEY: MOD_RES
<222> LOCATION: (4)
<223> OTHER INFORMATION: Nle
<223> OTHER INFORMATION: Description of Artificial Sequence:
      Norleu4-AIII

<400> SEQUENCE: 46

Arg Val Tyr Xaa Leu His Pro Phe
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Acpc3-AII
<221> NAME/KEY: MOD_RES
<222> LOCATION: (3)
<223> OTHER INFORMATION: 1-aminocyclopentane carboxylic acid

<400> SEQUENCE: 47

-continued

```
Asp Arg Xaa Tyr Ile His Pro Phe
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Orn2-AII
<221> NAME/KEY: MOD_RES
<222> LOCATION: (2)
<223> OTHER INFORMATION: Orn

<400> SEQUENCE: 48

Asp Xaa Val Tyr Ile His Pro Phe
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Citron2-AII
<221> NAME/KEY: MOD_RES
<222> LOCATION: (2)
<223> OTHER INFORMATION: Citron

<400> SEQUENCE: 49

Asp Xaa Val Tyr Ile His Pro Phe
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:
      Pro3Ala4-AII(1-7)

<400> SEQUENCE: 50

Asp Arg Pro Ala Ile His Pro
  1               5
```